(12) United States Patent
Wolters et al.

(10) Patent No.: US 8,786,850 B2
(45) Date of Patent: Jul. 22, 2014

(54) ILLUMINATION ENERGY MANAGEMENT IN SURFACE INSPECTION

(71) Applicant: KLA-Tencor Corporation, Milpitas, CA (US)

(72) Inventors: Christian Wolters, San Jose, CA (US); Aleksey Petrenko, Milpitas, CA (US); Kurt L. Haller, Pleasanton, CA (US); Juergen Reich, Campbell, CA (US); Zhiwei Xu, Sunnyvale, CA (US); Stephen Biellak, Sunnyvale, CA (US); George Kren, Los Alto Hills, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/662,626

(22) Filed: Oct. 29, 2012

(65) Prior Publication Data

US 2014/0118729 A1 May 1, 2014

(51) Int. Cl.
  *G01N 21/00* (2006.01)
  *G01N 21/88* (2006.01)
  *G01B 11/00* (2006.01)

(52) U.S. Cl.
  USPC .............. 356/237.5; 356/237.4; 356/614

(58) Field of Classification Search
  USPC .................. 356/237.1–237.5, 601–625
  See application file for complete search history.

(56) References Cited

U.S. PATENT DOCUMENTS

| | | | | |
|---|---|---|---|---|
| 6,091,075 | A * | 7/2000 | Shibata et al. | 250/559.44 |
| 6,127,689 | A * | 10/2000 | Pryor et al. | 250/559.29 |
| 6,201,601 | B1 * | 3/2001 | Vaez-Iravani et al. | 356/237.4 |
| 6,271,916 | B1 * | 8/2001 | Marxer et al. | 356/237.3 |
| 6,330,059 | B1 * | 12/2001 | Ishiguro et al. | 356/237.5 |
| 6,381,356 | B1 * | 4/2002 | Murakami et al. | 382/141 |
| 6,536,577 | B2 * | 3/2003 | Ishida et al. | 194/217 |
| 7,110,106 | B2 * | 9/2006 | Xu et al. | 356/237.5 |
| 7,495,191 | B2 * | 2/2009 | Chen | 219/121.73 |
| 7,548,308 | B2 * | 6/2009 | Mcmillan et al. | 356/237.2 |
| 7,630,087 | B2 * | 12/2009 | Verstappen et al. | 356/601 |
| 2001/0052975 | A1 * | 12/2001 | Biellak et al. | 356/237.3 |
| 2005/0094136 | A1 * | 5/2005 | Xu et al. | 356/237.3 |
| 2006/0274304 | A1 * | 12/2006 | Haller et al. | 356/237.1 |
| 2008/0079932 | A1 * | 4/2008 | Yokota | 356/237.1 |
| 2009/0116004 | A1 * | 5/2009 | Miller et al. | 356/237.4 |
| 2012/0229802 | A1 * | 9/2012 | Wolters et al. | 356/237.5 |

\* cited by examiner

*Primary Examiner* — Sang Nguyen
(74) *Attorney, Agent, or Firm* — Suiter Swantz pc llo (57) ABSTRACT

The disclosure is directed to a system and method of managing illumination energy applied to illuminated portions of a scanned wafer to mitigate illumination-induced damage without unnecessarily compromising SNR of an inspection system. The wafer may be rotated at a selected spin frequency for scanning wafer defects utilizing the inspection system. Illumination energy may be varied over at least one scanned region of the wafer as a function of radial distance of an illuminated portion from the center of the wafer and the selected spin frequency of the wafer. Illumination energy may be further applied constantly over one or more scanned regions of the wafer beyond a selected distance from the center of the wafer.

28 Claims, 7 Drawing Sheets

ILLUMINATION ENERGY MANAGEMENT IN SURFACE INSPECTION

TECHNICAL FIELD

The present disclosure generally relates to the field of inspection systems and more particularly to systems and methods of illumination energy management for inspection systems.

BACKGROUND

Inspection systems are often utilized in production and/or testing of semi-conductor devices. An inspection system may include an illumination system configured to illuminate at least a portion of a semi-conductor wafer. The inspection system may scan for wafer defects or impurities by detecting illumination reflected from the illuminated portion of the wafer. In some instances, illumination delivered to the illuminated portion of the wafer may cause undesired thermal and/or photochemical damage to the wafer.

Reducing an energy level of illumination delivered to the illuminated portion of the wafer may mitigate thermal/photochemical damage. However, reducing the energy level of illumination delivered to the illuminated portion of the wafer may undesirably affect signal-to-noise ratio (SNR) of illumination detected by the inspection system, thereby limiting resolving power and/or accuracy of the inspection system. Accordingly, systems and methods of illumination energy management are desired to mitigate illumination-induced wafer damage while maintaining acceptable SNR of the inspection system.

SUMMARY

The present disclosure is directed to illumination energy management for an inspection system to mitigate thermal/photochemical damage caused by illumination utilized to scan at least a portion of a wafer surface.

In one aspect, the present disclosure is directed to a system for managing illumination energy applied to a surface of a wafer. The system may include a sample stage configured to receive a wafer. The system may further include a motor mechanically coupled to the sample stage. The motor may be configured to actuate the sample stage to rotate the wafer at a selected spin frequency. The system may further include an illumination system including at least one illumination source configured to provide illumination along an illumination path to a surface of a wafer. The illumination system may be configured to illuminate a first portion of the wafer with illumination having a first energy level. The illumination system further configured to illuminate a second portion of the wafer with illumination having a second energy level. At least one of the first energy level or the second energy level may be determined utilizing a radial distance of an illuminated portion of the wafer measured from the center of the wafer and the selected spin frequency. For example, at least one of the first or second energy levels may be proportional to the radial distance of the illumination portion of the wafer and the selected spin frequency (i.e. $P \propto (rf)$, where $P$=energy level, $r$=radial distance, and $f$=spin frequency).

In another aspect, the present disclosure is directed to a method of managing illumination energy applied to a surface of a wafer. The method may include the steps of: receiving a wafer; rotating the wafer at a selected spin frequency; illuminating a first portion of the wafer with illumination having a first energy level; and illuminating a second portion of the wafer with illumination having a second energy level, wherein at least one of the first energy level or the second energy level is determined utilizing a radial distance of an illuminated portion of the wafer from the center of the wafer and the selected spin frequency.

In another aspect, the present disclosure is directed to a method of managing illumination energy applied to a surface of a wafer. The method may include the steps of: receiving a wafer; rotating the wafer at a selected spin frequency; illuminating a first portion of the wafer with illumination having a first energy level determined utilizing a first radial distance of the first portion of the wafer from the center of the wafer and the selected spin frequency, wherein the first portion of the wafer is less than a selected radial distance from the center of the wafer; illuminating a second portion of the wafer with illumination having a second energy level determined utilizing a second radial distance of the second portion of the wafer from the center of the wafer and the selected spin frequency, wherein the second portion of the wafer is less than the selected radial distance from the center of the wafer; and illuminating a third portion of the wafer with illumination having a third energy level, wherein the third portion of the wafer is greater than the selected radial distance from the center of the wafer.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1A:
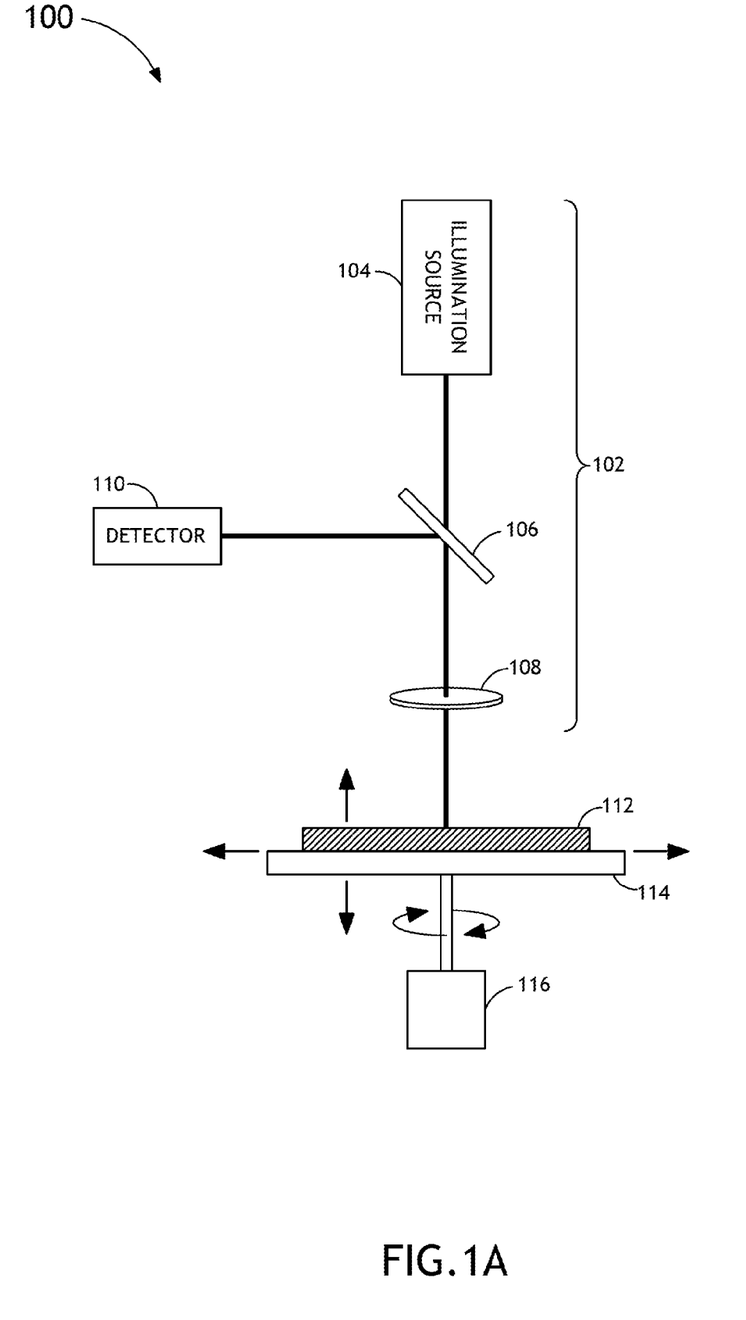
FIG. 1A is a block diagram illustrating an inspection system including an illumination system for illuminating a portion of a wafer, in accordance with an embodiment of this disclosure.
Figure 1B:
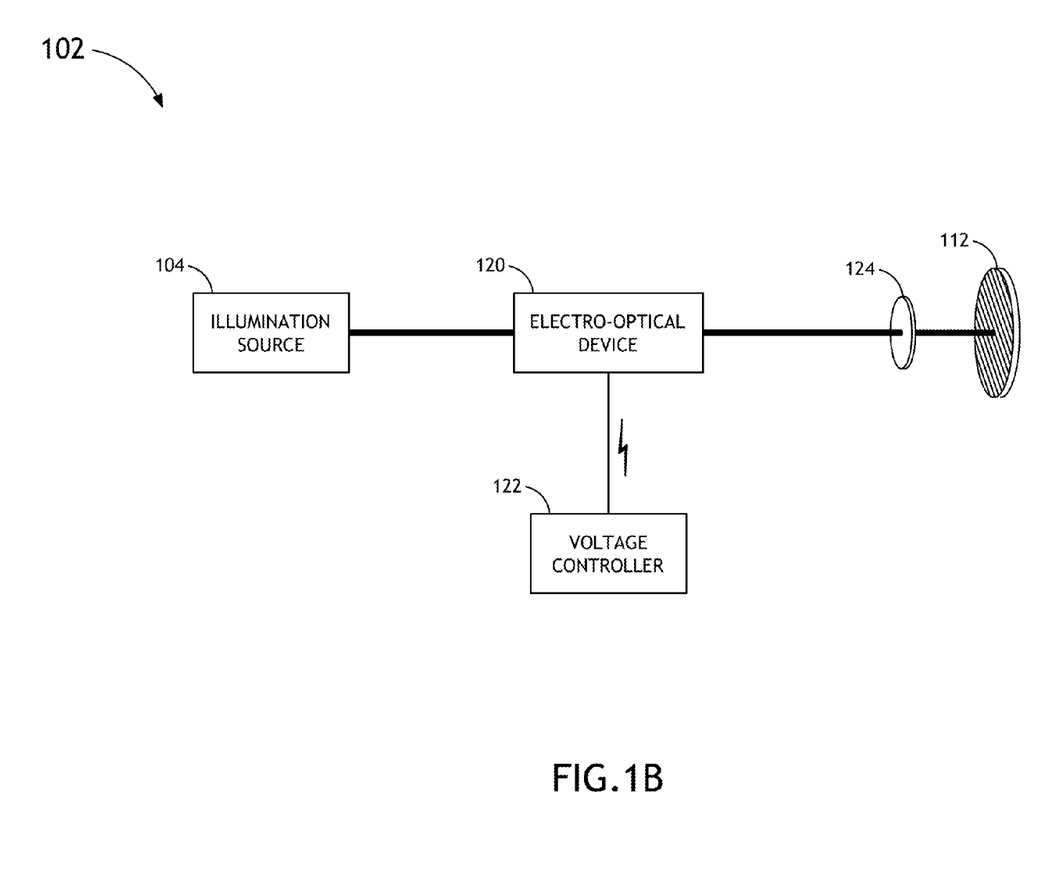
FIG. 1B is a block diagram illustrating the illumination system, wherein the illumination system includes at least one electro-optical device for managing an energy level of illumination delivered to the illuminated portion of the wafer, in accordance with an embodiment of this disclosure.
Figure 1C:
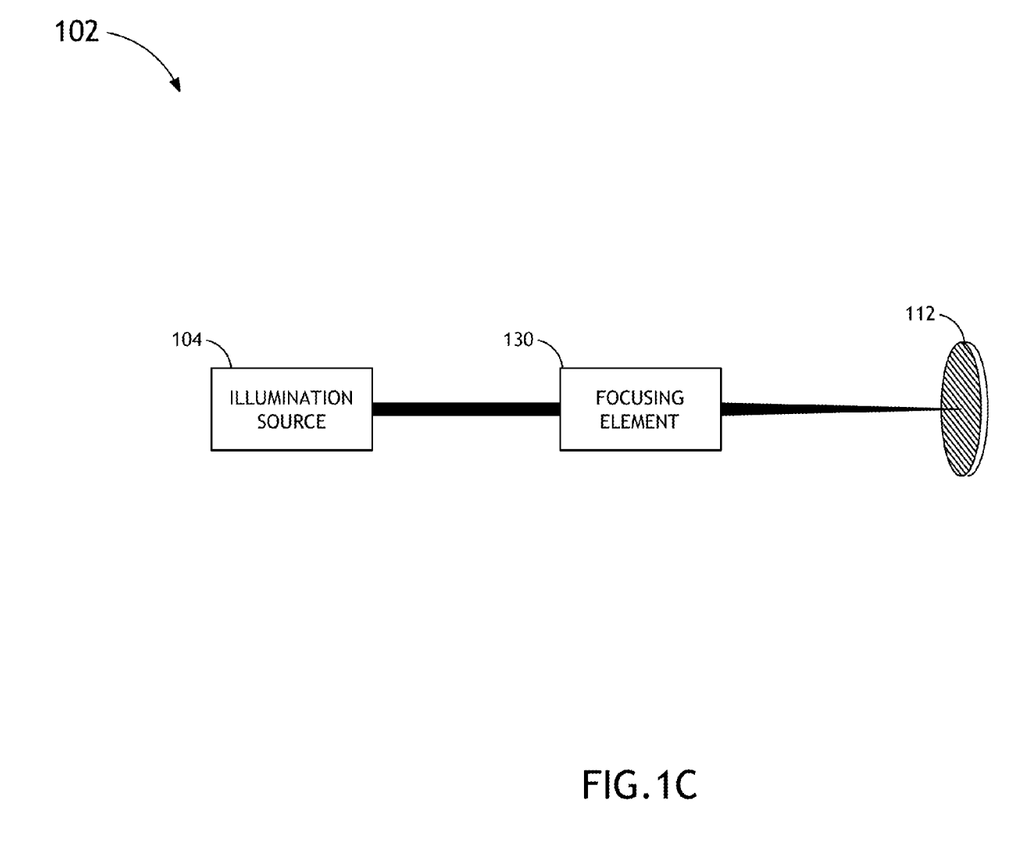
FIG. 1C is a block diagram illustrating the illumination system, wherein the illumination system includes at least one focusing element for managing an energy level of illumination delivered to the illuminated portion of the wafer, in accordance with an embodiment of this disclosure.
Figure 1D:
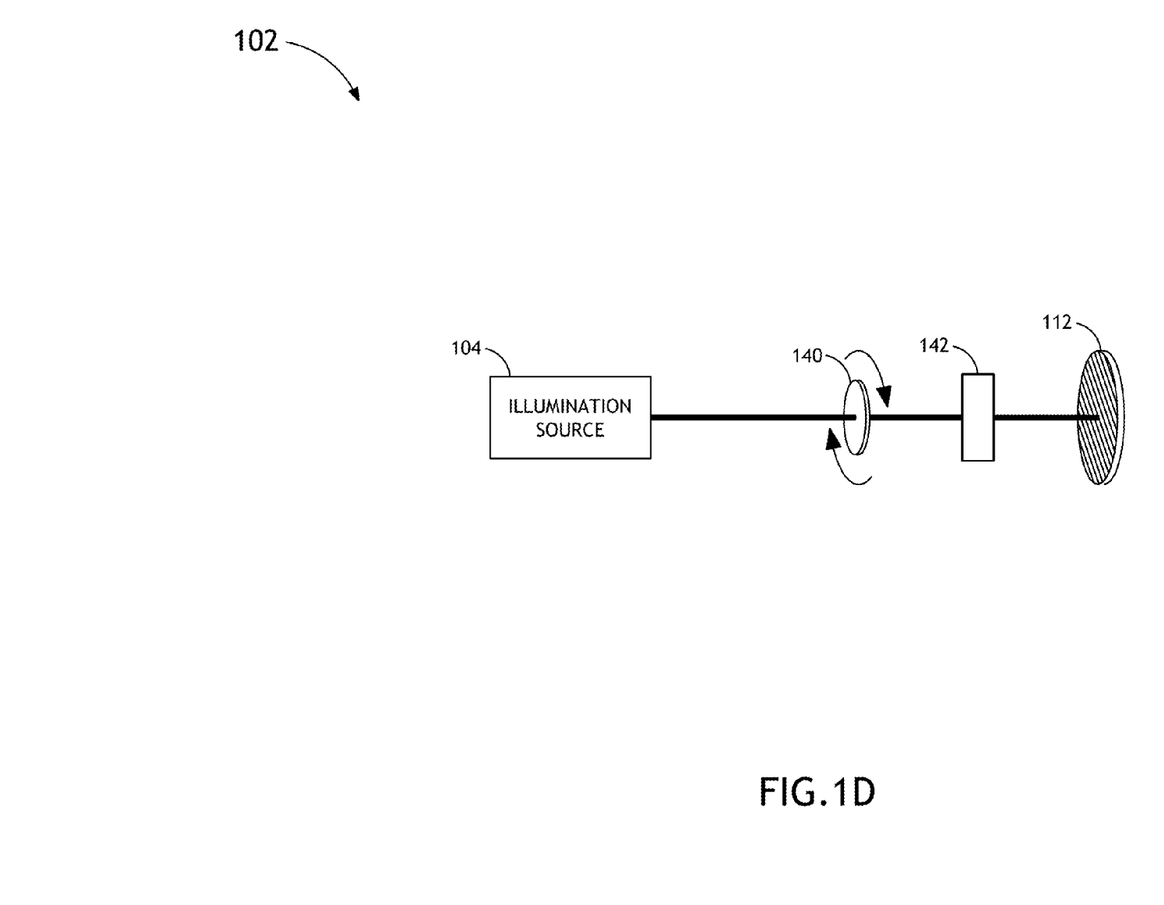
FIG. 1D is a block diagram illustrating the illumination system, wherein the illumination system includes at least one waveplate and at least one polarization element for managing an energy level of illumination delivered to the illuminated portion of the wafer, in accordance with an embodiment of this disclosure.
Figure 1E:
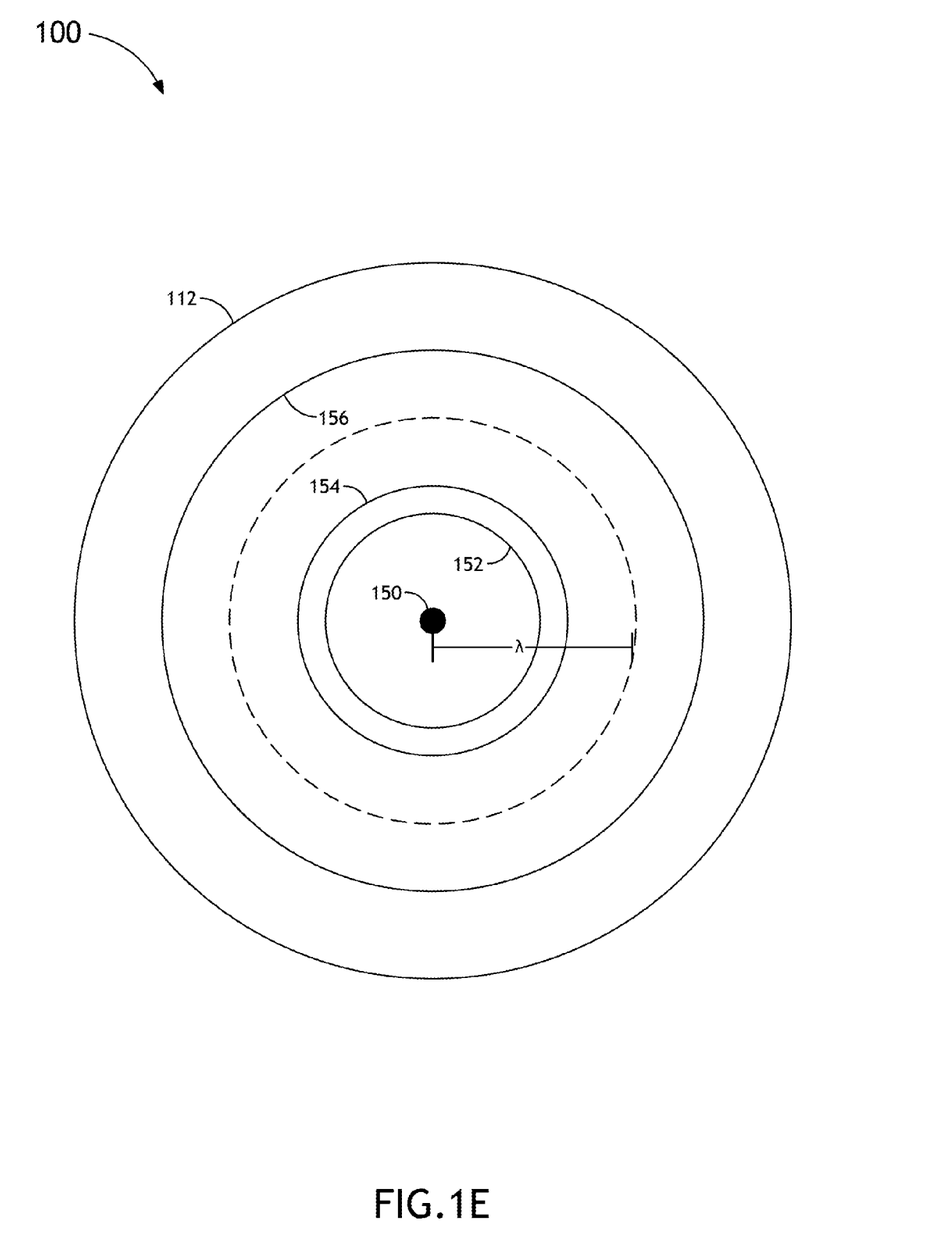
FIG. 1E is a conceptual view of a surface of the wafer illustrating a first portion of the wafer having a first radial distance from the center of the wafer and at least one additional portion of the wafer having at least one additional radial distance from the center of the wafer, in accordance with an embodiment of this disclosure.
Figure 2:
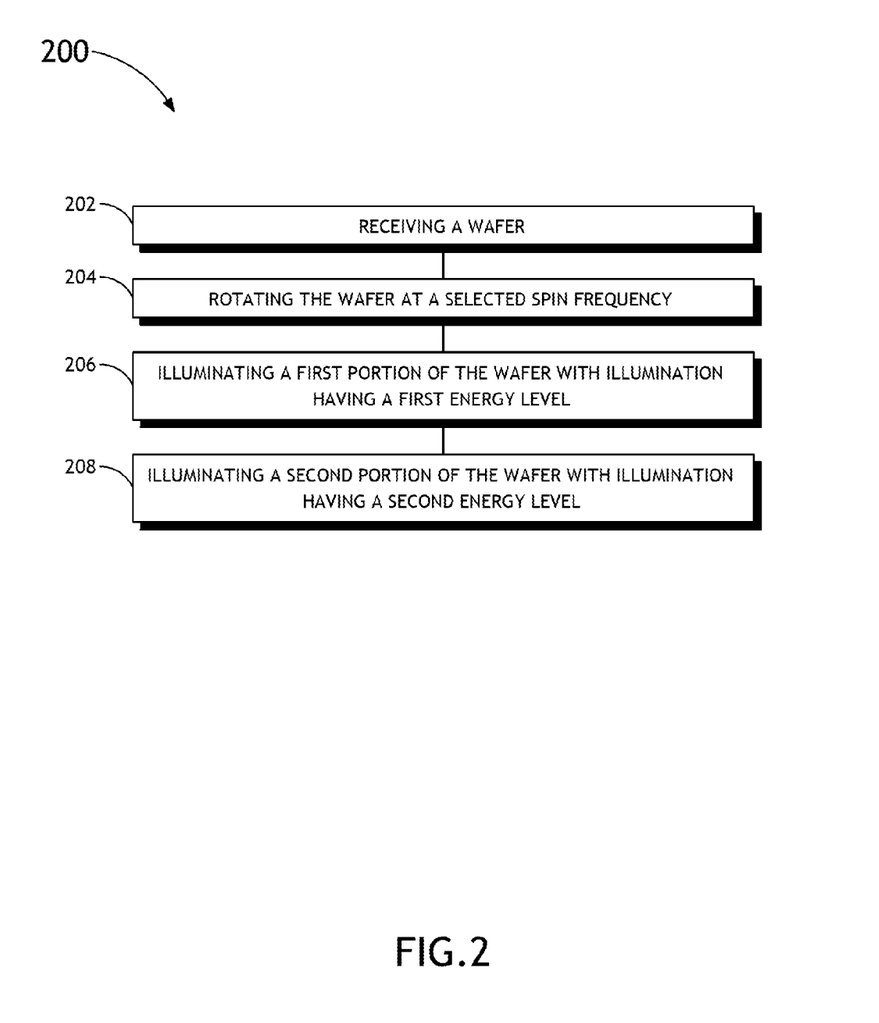
FIG. 2 is a flow diagram illustrating a method of managing illumination energy applied to a surface of a wafer, in accordance with an embodiment of this disclosure.
Figure 3:
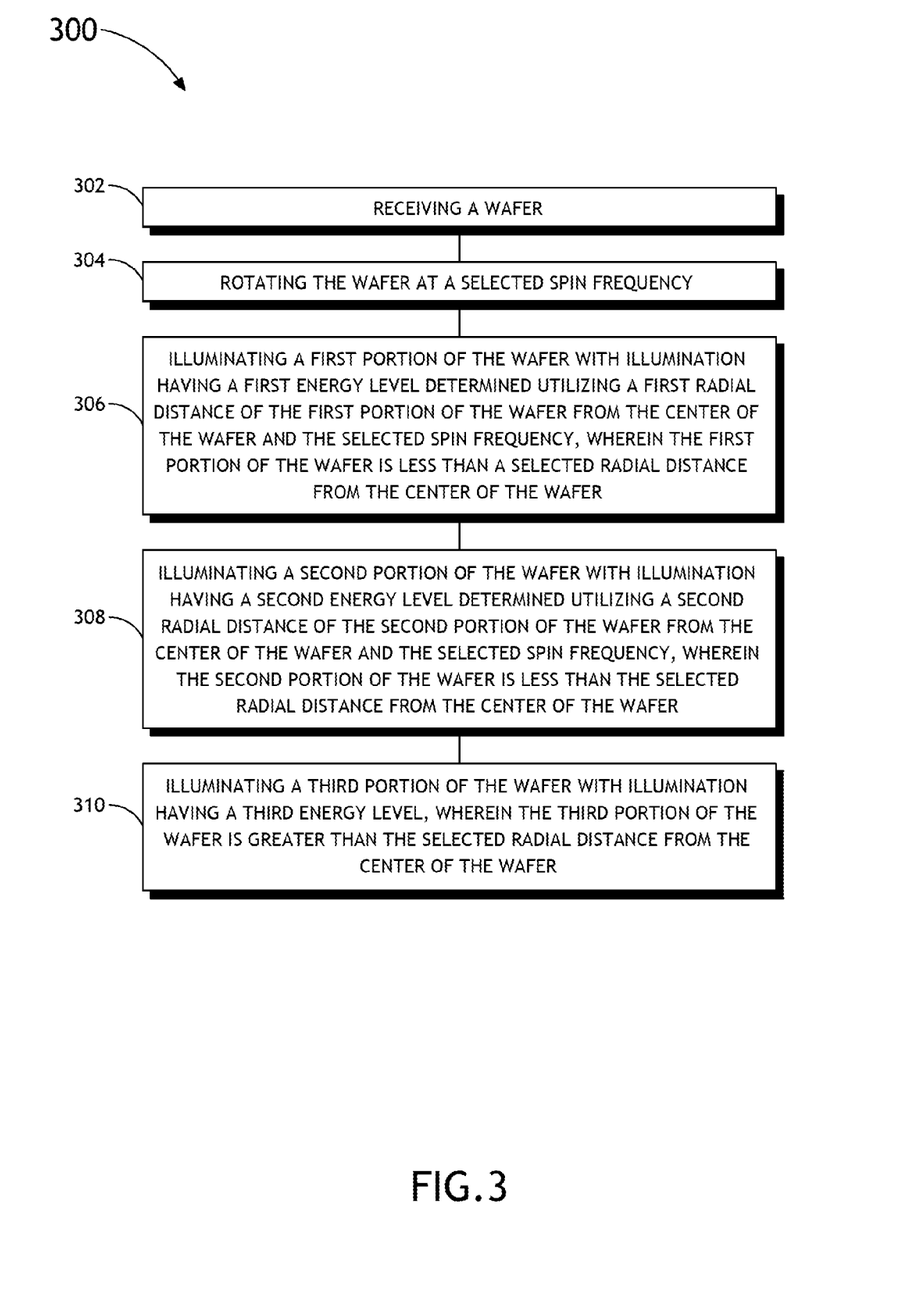
FIG. 3 is a flow diagram illustrating a method of managing illumination energy applied to a surface of a wafer, in accordance with an embodiment of this disclosure.

FIGS. 1 through 3 generally illustrate a system and method of managing illumination energy applied to a surface of a sample, such as a semi-conductor wafer. An inspection system may operate by scanning across at least a portion of a surface of a wafer with illumination to locate and/or analyze defects of the wafer. The wafer may be rotated and/or translated to enable scanning across the substantial entirety of the wafer or across at least an annular or disk-shaped region of the wafer. Illumination-induced thermal and/or photochemical damage (hereinafter "damage") may occur at inner regions of the wafer, since velocity of an illuminated portion of the wafer may decrease as scanning illumination approaches the center of the wafer. For example, an illuminated portion having a lower velocity may receive a higher dose of illumination energy than an illuminated portion having a relatively higher velocity as a result of illumination applied to the lower velocity illuminated portion for a longer time interval.

Wafer damage may be mitigated by decreasing an energy level of illumination delivered to the illuminated portion of the wafer at inner regions of the wafer. However, decreasing the energy level of illumination may undesirably affect signal-to-noise ratio (SNR) of the inspection system. Accordingly, the present disclosure provides a system and method of managing illumination energy for an inspection system to maintain acceptable SNR while mitigating damage caused by illumination delivered to the illuminated portion of the wafer.

As illustrated in FIG. 1A, an inspection system 100 may include an illumination system 102 configured to illuminate at least a portion of a surface of a wafer 112. The illumination system 102 may include at least one illumination source 104 configured to deliver illumination to the illuminated portion of the wafer 112 along an illumination path. The illumination path may include a direct line of sight from the illumination source 104 to the illuminated portion of the wafer 112. Alternatively, the illumination path may be delineated by one or more optical elements configured to direct illumination from the illumination source 104 along a selected path to the illuminated portion of the wafer 112. For example, the illumination system 102 may include at least one focusing lens 108 configured to focus illumination delivered to the illuminated portion of the wafer 112.

The inspection system 100 may further include at least one detector 110 configured to receive at least a portion of reflected illumination from the illuminated portion of the wafer 112. The detector 110 may include a photodiode, photodiode array, camera, or any other photo-detector known to the art for detecting illumination. In one embodiment, the detector 110 may be configured to receive reflected illumination from a detection path delineated by at least one optical element, such as a beam splitter 106, configured to direct at least a portion of reflected illumination from the illuminated portion of the wafer 112 along a selected path to the detector 110.

The detector 110 may be communicatively coupled to at least computing system including at least one processor configured to execute program instructions from carrier media, such as a HDD, SSD, flash memory, optical disc, magnetic disc, magnetic tape, RAM, or any other permanent or semi-permanent data storage. The computing system may be configured to receive information (e.g. intensity, polarity, wavelength, etc.) associated with detected illumination from the detector 110. The computing system may be further configured to determine defect characteristics (e.g. location, size, defect type, etc.) of the wafer utilizing information associated with detected illumination.

In one embodiment, the inspection system 100 may be configured for scanning across at least one region of the wafer 112 to locate and/or analyze wafer defects. The inspection system 100 may include a sample stage 114 configured to receive the wafer 112. The inspection system 100 may further include one or more actuators 116 mechanically coupled to the sample stage 114. For example, the actuator 116 may include a motor configured to rotate the wafer 112 at a selected spin frequency for scanning. In one embodiment, the actuator 116 may further include an actuation arm configured actuate the sample stage 114 sideways to translate the scanned region of the rotated wafer 112 through illumination delivered by the illumination system 102. The actuation arm may be further configured to actuate the sample stage towards and/or away from the illumination system to adjust focus of illumination delivered to the illuminated portion of the wafer 112.

The foregoing embodiments are of an exemplary nature; however the inspection system 100 may include any combination of components and/or configurations known to the art, such as those described in U.S. Pat. No. 7,548,308, U.S. Pat. No. 6,271,916, and U.S. Pat. No. 6,201,601, all incorporation herein by reference. The inspection system 100 may further include one or more means for managing an energy level of illumination delivered to the illuminated portion of the wafer 112. Several means of managing the energy level of illumination delivered to the illuminated portion of the wafer 112 are known the art, such as systems and/or methods described in U.S. Pat. No. 7,548,308, all incorporated herein by reference. For example the illumination system 102 may include one or more filters configured to adjust illumination energy. Alternatively, the energy level of illumination delivered to the illuminated portion of the wafer 112 may be affected by varying the rotational speed of the wafer 112 utilizing the actuator 116 to adjust the selected spin frequency of the sample stage 114. Several alternative means of managing illumination energy for the inspection system 100 are further illustrated by the following embodiments.

In one embodiment, the actuator 116 may be configured to translate the sample stage 114 relative to the illumination system 102 at a selected speed to control the scan pitch of illumination over the scanned region of the wafer 112. The actuator 116 may be configured to control the energy level of illumination delivered to illuminated portions of the wafer 112 by continuously varying the scan pitch. In another embodiment, the actuator 116 may be configured to actuate the sample stage 114 relative to the illumination system 102 to affect focus of illumination delivered to the illuminated portion of the wafer 112. The actuator 116 may be configured to control the energy level of illumination delivered to illuminated portions of the wafer 112 by continuously varying the focus level over the scanned region of the wafer 112.

In an embodiment, the illumination system 102 may include at least one energy controller, such as an opto-mechanical, electrical, and/or electro-optical device, configured for controlling the energy level of illumination delivered to the illuminated portion of the wafer 112. FIG. 1B illustrates an exemplary embodiment of the illumination system 102, wherein the illumination system 102 may include at least one electro-optical device 120, such as a Pockets cell, disposed along the illumination path. The electro-optical device 120 may be configured to attenuate illumination received directly or indirectly from the illumination source 104 to control the energy level of illumination delivered to the illuminated portion of the wafer 112. The electro-optical device 120 may be configured to attenuate received illumination by a selected attenuation in response to an applied voltage signal from a communicatively coupled voltage controller 122. The voltage controller 122 may be configured to continuously vary applied voltage to provide continuously varying attenuation of illumination delivered to illuminated portions of the wafer 112 over the scanned region of the wafer. In a further embodiment, the illumination system 102 may further include at least one attenuating optical element 124 disposed along the illumination path in series with the electro-optical illumination device 120. The attenuating optical element 124 may be configured to attenuate illumination received directly or indirectly from the illumination source 104 by a fixed attenuation to allow a broader range of total attenuation.

In a further embodiment, the energy controller of the illumination system 102 may be integrated within the illumination source 104. For example, the illumination source 104 may include a semi-conductor diode laser driven by a variable current. The foregoing examples are included for illustrative purposes only. It is contemplated that any energy controller for internally or externally controlling the energy level of illumination emanating from the illumination source 104 may be utilized to achieve the functionality described herein.

FIG. 1C illustrates another exemplary embodiment of the illumination system 102, wherein the illumination system 102 may include at least one focusing element 130 disposed along the illumination path. The focusing element 130 may include at least one refractive element, such as a radially symmetric lens, a cylindrical lens, an astigmatic lens, an anamorphic prism pair, a multi-element lens assembly, and the like. Alternatively the focusing element 130 may include any other system or device known to the art for adjusting focus of illumination, such as a zooming lens assembly. The focusing element 130 may be configured to control the energy level of illumination delivered to the illumination portion of the wafer 112 by varying spot size of delivered illumination. The focusing element 130 may be configured to vary spot size of illumination delivered to illuminated portions of the wafer 112 continuously over the scanned region of the wafer 112.

FIG. 1D illustrates yet another exemplary embodiment of the illumination system 102, wherein the illumination system 102 may include at least one waveplate 140, such as a half-wave plate, disposed along the illumination path in series with at least one polarization element 142, such as a polarizer or analyzer. The illumination system 102 may further include at least one motor mechanically coupled to the waveplate 140. The motor may be configured to rotate the waveplate 140 by a selected rotation relative to the polarization element 142 to attenuate illumination directed along the illumination path through the waveplate 140 and the polarization element 142 by a selected attenuation. In another embodiment, a motor may be mechanically coupled to the polarization element 142. In either case, the illumination system 102 may be configured to control the energy level of illumination delivered to the illumination portion of the wafer 112 by rotating at least one of the wavepate 140 or the polarization element 142 to provide the selected attenuation. Accordingly, the illumination system 102 may be configured to continuously vary the energy level of illumination delivered to illuminated portions of the wafer 112 over the scanned region of the wafer 112.

The inspection system 100 may include one or more of the foregoing means of managing illumination energy and/or any alternative means now or hereafter known to the art. A desired energy level of illumination delivered to the illuminated portion of the wafer 112 may be associated with a radial distance of the illuminated portion from the center of the wafer 112 and the selected spin frequency of the wafer 112. For example the desired energy level may be proportional to the radial distance of the illuminated portion and the selected spin frequency (i.e. $P \propto (rf)$, where P=energy level, r=radial distance, and f=spin frequency). The desired energy level may be further associated with a maximum energy level of illumination that can be delivered to the illuminated portion of the wafer 112 without causing damage to the wafer 112 and tangential spot size and radial spot size of illumination delivered to the illuminated portion of the wafer 112 (i.e. $P \propto P_D * S_R * S_T$, where $P_D$=max energy level, $S_R$=radial spot size, and $S_T$=tangential spot size).

The illumination system 102 may be configured to illuminate a plurality of portions over the scanned region of the wafer 112 with illumination having a plurality of desired energy levels. Accordingly, the illumination system 102 may be configured to mitigate wafer damage while scanning across at least one region of the wafer 112 with acceptable SNR. In one embodiment, the illumination system 102 may be further configured for scanning across at least one region of the wafer at a constant SNR by continuously adjusting energy level of illumination delivered to illuminated portions of the wafer 112. As illustrated in FIG. 1E, the illumination system 102 may be configured to illuminate a first portion 152 of the wafer 112 with illumination having a first energy level, a second portion 154 of the wafer 112 with illumination having a second energy level 156, a third portion of the wafer 112 with illumination having a third energy level, and so on. The energy level of illumination delivered to illuminated portions of the wafer 112 at any given time may be further managed via the inspection system 100 or any other means known to the art, in accordance with methods 200 and 300 described herein.

FIG. 2 illustrates method 200 of managing illumination energy applied to illuminated portions of the surface of the wafer 112 being scanned by the inspection system 100. At step 202, the sample stage 114 of the inspection system may receive the wafer 112. At step 204, the actuator 116 may actuate the sample stage 114 to rotate the wafer 112 at the selected spin frequency for scanning by the inspection system 100. At steps 206 and 208, the illumination system 102 may illuminate scanned portions of the rotated wafer 112 with varying energy levels of illumination across at least one scanned region of the surface of the wafer 112. For example, the illumination system 102 may illuminate a first scanned portion 152 of the wafer 112 with illumination having a first energy level at step 206, a second scanned portion 154 of the wafer 112 with illumination having a second energy level at step 208, and so on. In one embodiment, the illumination system 102 may vary illumination energy delivered to illuminated portions of the wafer 112 in proportion to the radial distance of the illuminated portion from the center 150 of the wafer 112 and the selected spin frequency.

In an embodiment, the illumination system 102 may continuously vary the energy level of illumination delivered to illuminated portions across one or more regions of the wafer 112. For example, the energy level of illumination delivered across a region may be continuously ramped up or down. Alternatively, the illumination system 102 may discretely vary the energy level of illumination delivered to illuminated portions across one or more regions of the wafer 112. For example, the energy level of illumination delivered across a region may be incrementally stepped up or down. Furthermore, the illumination system 102 may apply a hybrid approach to vary the energy level of illumination continuously over at least one region and provide illumination at a constant energy level or a plurality of discrete energy levels over at least one additional region of the wafer 112.

FIG. 3 illustrates method 300 of managing illumination energy applied to illuminated portions of the surface of the wafer 112 by varying the energy level of delivered illumination over at least one scanned region including portions less than a selected radial distance $\lambda$ from the center 150 of the wafer 112 and applying at least one selected energy level of illumination over at least one additional scanned region including portions greater than the selected radial distance $\lambda$ from the center 150 of the wafer 112. At step 302, the sample stage 114 of the inspection system may receive the wafer 112. At step 304, the actuator 116 may actuate the sample stage 114 to rotate the wafer 112 at the selected spin frequency for scanning by the inspection system 100. At steps 306 and 308, the illumination system 102 may illuminate scanned portions of the rotated wafer 112 less than the selected radial distance $\lambda$ from the center 150 with varying energy levels. For example, at step 306, the illumination system 102 may illuminate a first scanned portion 152 of the wafer 112 with illumination having a first energy level determined as a function of the radial distance of the first portion 152 from the center 150 and the selected spin frequency, wherein the first portion 152 is less than the selected distance $\lambda$ from the center 150 of the wafer 112. Similarly, at step 308, the illumination system 102 may illuminate a second scanned portion 154 of the wafer 112 with illumination having a second energy level determined as a function of the radial distance of the second portion 154 from the center 150 and the selected spin frequency, wherein the second portion 154 is less than the selected distance $\lambda$ from the center 150 of the wafer 112, and so on. At step 310, the illumination system 102 may illuminate a third portion 156 of the wafer 112 greater than the selected distance $\lambda$ from the center 150 with illumination having a selected energy level, such as a maximum energy level or an energy level associated with a desired SNR. The illumination system 102 may similarly illuminate one or more scanned portions of the wafer 112 greater than the selected distance $\lambda$ from the center 150 with illumination having the selected energy level. In one embodiment, the illumination system 102 may accordingly provide varying illumination energy over a first scanned region of the wafer 112 and constant illumination energy over a second scanned region of the wafer 112 to achieve desired sensitivity while mitigating wafer damage.

It is further contemplated that each of the embodiments of the method described above may include any other step(s) of any other method(s) described herein. In addition, each of the embodiments of the method described above may be performed by any of the systems described herein.

It should be recognized that the various steps described throughout the present disclosure may be carried out by a single computing system or, alternatively, a multiple computing system. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

The computing system may include, but is not limited to, a personal computing system, mainframe computing system, workstation, image computer, parallel processor, or any other device known in the art. In general, the term "computing system" may be broadly defined to encompass any device having one or more processors, which execute instructions from a memory medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier medium. The carrier medium may be a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for managing illumination energy applied to a surface of a wafer, comprising:
   a sample stage configured to receive a wafer;
   a motor mechanically coupled to the sample stage, the motor configured to actuate the sample stage to rotate the wafer at a selected spin frequency; and
   an illumination system configured to:
      illuminate a first portion of the wafer with illumination having a first energy level, wherein the first portion of the wafer is less than a selected radial distance from the center of the wafer, wherein the first energy level is at least partially based upon the selected spin frequency and at least partially based upon a radial distance of the first portion of the wafer from the center of the wafer;
      illuminate a second portion of the wafer with illumination having a second energy level, wherein the second portion of the wafer is less than the selected radial distance from the center of the wafer, wherein the second energy level is at least partially based upon the selected spin frequency and at least partially based upon a radial distance of the second portion of the wafer from the center of the wafer; and
      illuminate a third portion of the wafer with illumination having a third energy level, wherein the third portion of the wafer is greater than the selected radial distance from the center of the wafer.

2. The system of claim 1, wherein at least one of the first energy level or the second energy level is proportional to the radial distance of the illuminated portion of the wafer and the selected spin frequency.

3. The system of claim 1, wherein the illumination system includes at least one energy controller configured to attenuate an energy level of illumination delivered to the illuminated portion of the wafer by a selected attenuation, wherein the at least one energy controller includes at least one of an opto-mechanical device, an electrical device, or an electro-optical device.

4. The system of claim 3, wherein the at least one energy controller includes a Pockets cell.

5. The system of claim 3, wherein the illumination system further includes at least one optical element configured to attenuate the energy level of illumination delivered to the illuminated portion of the wafer by a fixed attenuation.

6. The system of claim 1, wherein the illumination system includes at least one focusing element configured to control spot size of illumination delivered to the illuminated portion of the wafer, wherein spot size is associated with energy level of illumination delivered to the illuminated portion of the wafer.

7. The system of claim 6, wherein the at least one focusing element includes at least one refractive element.

8. The system of claim 7, wherein the at least one refractive element includes at least one of:
a radially symmetric lens, a cylindrical lens, an astigmatic lens, an anamorphic prism pair, or a multi-element lens assembly.

9. The system of claim 6, wherein the at least one focusing element includes at least one zoom lens assembly.

10. The system of claim 1, wherein the illumination system includes:
a waveplate;
a polarization element; and
at least one motor mechanically coupled to at least one of the waveplate or the polarization element, the at least one motor configured to rotate at least one of the waveplate or the polarization element to control an energy level of illumination directed through the waveplate and the polarization element to the illuminated portion of the wafer.

11. The system of claim 1, wherein the system further includes:
an actuation arm mechanically coupled to the sample stage, the actuation arm configured to actuate the sample stage relative to the illumination system to control focus level of illumination delivered to the illuminated portion of the wafer, wherein focus level is associated with an energy level of illumination delivered to the illuminated portion of the wafer.

12. The system of claim 1, wherein the system further includes:
an actuation arm mechanically coupled to the sample stage, the actuation arm configured to actuate the sample stage relative to the illumination system to control scan pitch of illumination delivered to the illuminated portion of the wafer, wherein scan pitch is associated with an energy level of illumination delivered to the illuminated portion of the wafer.

13. A method of managing illumination energy applied to a surface of a wafer, comprising:
receiving a wafer;
rotating the wafer at a selected spin frequency;
illuminating a first portion of the wafer with illumination having a first energy level, wherein the first energy level is at least partially based upon the selected spin frequency and at least partially based upon a radial distance of the first portion of the wafer from the center of the wafer; and
illuminating a second portion of the wafer with illumination having a second energy level, wherein the second energy level is at least partially based upon the selected spin frequency and at least partially based upon a radial distance of the second portion of the wafer from the center of the wafer.

14. The method of claim 13, wherein at least one of the first energy level or the second energy level is proportional to the radial distance of the illuminated portion of the wafer and the selected spin frequency.

15. The method of claim 13, wherein the method further includes:
attenuating an energy level of illumination delivered to the illuminated portion of the wafer by a selected attenuation.

16. The method of claim 15, wherein the method further includes:
attenuating the energy level of illumination delivered to the illuminated portion of the wafer by a fixed attenuation.

17. The method of claim 13, wherein the method further includes:
controlling spot size of illumination delivered to the illuminated portion of the wafer, wherein spot size is associated with energy level of illumination delivered to the illuminated portion of the wafer.

18. The method of claim 13, wherein the method further includes:
directing illumination through a waveplate and a polarization element to the illuminated portion of the wafer; and
rotating at least one of the waveplate or the polarization element to control an energy level of illumination delivered to the illuminated portion of the wafer.

19. The method of claim 13, wherein the method further includes:
disposing the wafer on a sample stage; and
actuating the sample stage relative to an illumination system to control focus level of illumination delivered from the illumination system to the illuminated portion of the wafer, wherein focus level is associated with an energy level of illumination delivered to the illuminated portion of the wafer.

20. The method of claim 13, wherein the method further includes:
disposing the wafer on a sample stage; and
actuating the sample stage relative to an illumination system to control scan pitch of illumination delivered from the illumination system to the illuminated portion of the wafer, wherein scan pitch is associated with an energy level of illumination delivered to the illuminated portion of the wafer.

21. A method of managing illumination energy applied to a surface of a wafer, comprising:
receiving a wafer;
rotating the wafer at a selected spin frequency;
illuminating a first portion of the wafer with illumination having a first energy level determined utilizing a first radial distance of the first portion of the wafer from the center of the wafer and the selected spin frequency, wherein the first portion of the wafer is less than a selected radial distance from the center of the wafer;
illuminating a second portion of the wafer with illumination having a second energy level determined utilizing a second radial distance of the second portion of the wafer from the center of the wafer and the selected spin frequency, wherein the second portion of the wafer is less than the selected radial distance from the center of the wafer; and illuminating a third portion of the wafer with illumination having a third energy level, wherein the third portion of the wafer is greater than the selected radial distance from the center of the wafer.

22. The method of claim 21, wherein at least one of the first energy level or the second energy level is proportional to a radial distance of an illuminated portion of the wafer from the center of the wafer and the selected spin frequency.

23. The method of claim 21, wherein the method further includes:

attenuating an energy level of illumination delivered to an illuminated portion of the wafer by a selected attenuation.

24. The method of claim 23, wherein the method further includes:

attenuating the energy level of illumination delivered to the illuminated portion of the wafer by a fixed attenuation.

25. The method of claim 21, wherein the method further includes:

controlling spot size of illumination delivered to an illuminated portion of the wafer, wherein spot size is associated with energy level of illumination delivered to the illuminated portion of the wafer.

26. The method of claim 21, wherein the method further includes:

directing illumination through a waveplate and a polarization element to an illuminated portion of the wafer; and rotating at least one of the waveplate or the polarization element to control an energy level of illumination delivered to the illuminated portion of the wafer.

27. The method of claim 21, wherein the method further includes:

disposing the wafer on a sample stage; and actuating the sample stage relative to an illumination system to control focus level of illumination delivered from the illumination system to an illuminated portion of the wafer, wherein focus level is associated with an energy level of illumination delivered to the illuminated portion of the wafer.

28. The method of claim 21, wherein the method further includes:

disposing the wafer on a sample stage; and actuating the sample stage relative to an illumination system to control scan pitch of illumination delivered from the illumination system to an illuminated portion of the wafer, wherein scan pitch is associated with an energy level of illumination delivered to the illuminated portion of the wafer.

* * * * *